(12) United States Patent
Yang et al.

(10) Patent No.: US 9,921,128 B2
(45) Date of Patent: Mar. 20, 2018

(54) METHOD AND APPARATUS FOR RESIDUAL STRESS MEASUREMENT THROUGH INDENTATION WITH IN-SITU GENERATED REFERENCE

(71) Applicant: Exponential Business And Technologies Company, Eden Prairie, MN (US)

(72) Inventors: Dehua Yang, Savage, MN (US); Ryan Farel, Shakopee, MN (US)

(73) Assignee: EXPONENTIAL BUSINESS AND TECHNOLOGIES COMPANY, Eden Prairie, MN (US)

( * ) Notice: Subject to any disclaimer, the term of this patent is extended or adjusted under 35 U.S.C. 154(b) by 325 days.

(21) Appl. No.: 14/671,725

(22) Filed: Mar. 27, 2015

(65) Prior Publication Data

US 2016/0282246 A1  Sep. 29, 2016

(51) Int. Cl.
G01N 3/42 (2006.01)
G01M 5/00 (2006.01)
G01N 3/40 (2006.01)

(52) U.S. Cl.
CPC .............. *G01M 5/00* (2013.01); *G01M 5/005* (2013.01); *G01N 3/40* (2013.01); *G01N 3/42* (2013.01);
(Continued)

(58) Field of Classification Search
CPC .................................. G01N 3/42; G01N 3/40
See application file for complete search history.

(56) References Cited

U.S. PATENT DOCUMENTS 4,276,087 A * 6/1981 Haswell .............. C22C 33/0278
75/243

6,013,333 A * 1/2000 Carson .................... C03C 17/30
427/224
(Continued)

FOREIGN PATENT DOCUMENTS

WO 2006071001 A1 7/2006
WO 2008096914 A1 8/2008

OTHER PUBLICATIONS

Bocciarelli et al. "Indentation and imprint mapping method for identification of residual stresses," Computational Materials Science, Apr. 2007, 39(2):381-392.
(Continued)

*Primary Examiner* — Paul West
(74) *Attorney, Agent, or Firm* — Vidas Arrett & Steinkraus

(57) ABSTRACT

Methods and apparatuses for measurement of residual stresses are provided. For example, a method includes indenting a first portion of a sample having residual stress and generating a residual stress reference zone at a second portion of the sample. Indenting and generating a residual stress reference zone may be performed in situ (e.g., on the same instrument platform, etc.). The present disclosure also provides a method for generating a residual stress reference, the method including providing a first sample having a residual stress and reducing the residual stress in at least a portion of the sample, wherein reducing the residual stress includes raster scanning wear, or exposure to laser energy, ion beam energy, electron beam microscopy, scanning probe microscopy, scanning electron microscopy, heat energy, vibration energy; and exposing the sample to ultrasonic energy. An apparatus includes an indenter device structured and arranged to indent a first portion of a sample and a reference-generating device structured and arranged to generate a residual stress reference zone (e.g., in situ) in the sample.

16 Claims, 5 Drawing Sheets

(52) U.S. Cl.
CPC ............ *G01N 2203/008* (2013.01); *G01N 2203/0286* (2013.01)

(56) References Cited

U.S. PATENT DOCUMENTS

| | | | | |
|---|---|---|---|---|
| 6,155,104 | A | * | 12/2000 | Suresh ............... G01N 3/42 73/789 |
| 6,311,135 | B1 | | 10/2001 | Suresh et al. |
| 6,568,250 | B1 | | 5/2003 | Sinha |
| 6,851,300 | B2 | | 2/2005 | Kwon et al. |
| 7,472,603 | B2 | | 1/2009 | Kim |
| 2007/0180924 | A1 | | 8/2007 | Warren et al. |
| 2007/0227236 | A1 | | 10/2007 | Bonilla et al. |
| 2008/0141782 | A1 | * | 6/2008 | Kim ................... G01N 3/42 73/823 |
| 2010/0064765 | A1 | | 3/2010 | Han et al. |
| 2010/0108884 | A1 | | 5/2010 | Lou et al. |

OTHER PUBLICATIONS

Faisal et al., "A Review of Patented Methodologies in Instrumented Indentation Residual Stress Measurements," May 2011, 4(2):138-152.

Jang et al., "Assessing welding residual stress in A335 P12 steel welds before and after stress-relaxation annealing through instrumented indentation technique," Scripta Materialia, Mar. 17, 2003; 48(6):743-748.

Jang, "Estimation of residual stress by instrumented indentation: A review," Journal of Ceramic Processing Research, 2009, 10(3):391-400.

Ponslet et al., "Residual Stress Measurement Using the Hole Drilling Method and Laser Speckle Interferometry Part III: Analysis Technique," Experimental Techniques, Sep./Oct. 2003; 27(5):45-48.

Suresh et al., "A New Method for Estimating Residual Stresses by Instrumented Sharp Indentation," Acta Materialia, Oct. 9, 1998; 46(16):5755-5767.

Vishay Precision Group, "Measurement of Residual Stresses by the Hole-Drilling Strain Gage Method," Tech Note TN-503, document No. 11053; revision: Nov. 1, 2010; www.micromeasurements.com; 19-33.

Xu et al., "Chapter 7: Residual Stress Determination Using Nanoindentation Technique," Micro and Nano Mechanical Testing of Materials and Devices; Editors: Yang et al.; Springer Science+Business Media, LLC, 2008; doi: 10.1007/978-0-387-78701-5, 139-153.

Xu et al., "Estimation of residual stresses from elastic recovery of nanoindentation," Philosophical Magazine, Jul. 1, 2006, 86(19):2835-2846.

Xu et al., "Influence of equi-biaxial residual stress on unloading behaviour of nanoindentation," Acta Materialia, Apr. 2005 53(7)1913-1919.

* cited by examiner

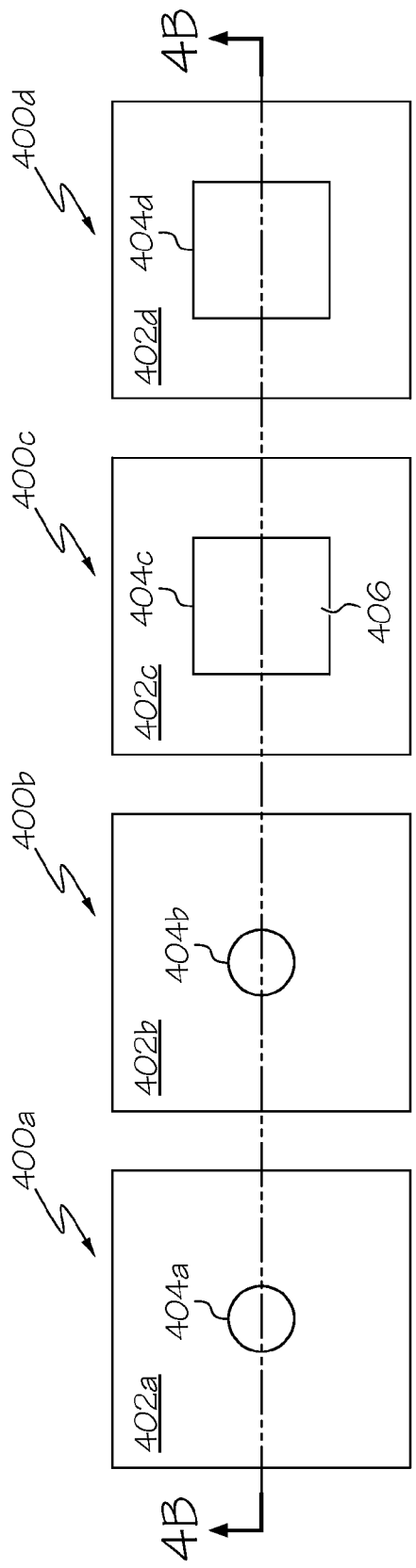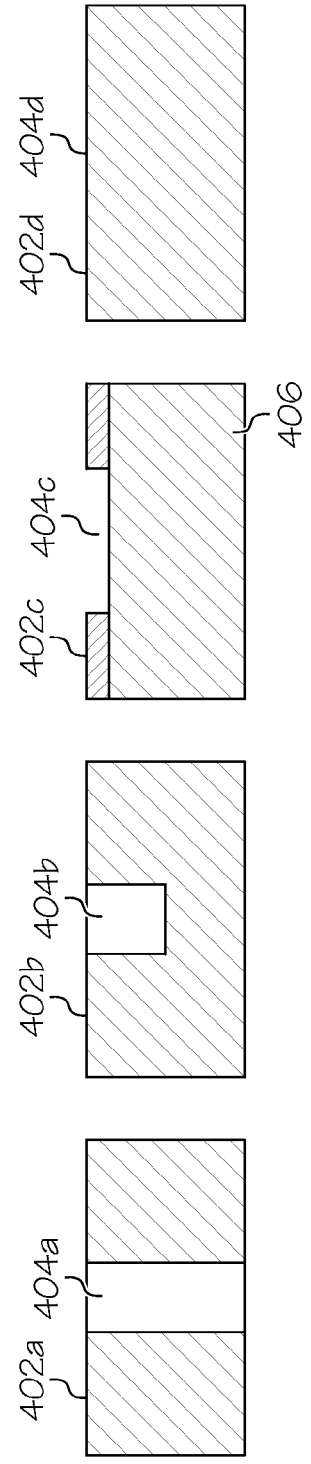
FIG. 4A
FIG. 4B

METHOD AND APPARATUS FOR RESIDUAL STRESS MEASUREMENT THROUGH INDENTATION WITH IN-SITU GENERATED REFERENCE

CROSS-REFERENCE TO RELATED APPLICATIONS

Not applicable.

STATEMENT REGARDING FEDERALLY SPONSORED RESEARCH

Not applicable.

BACKGROUND

The present disclosure relates generally to the field of methods and apparatus for measurement, testing, and evaluation of residual stresses of various materials using, for example, indentation.

Various types of systems for measuring material properties (e.g., hardness, residual stress, elastic modulus, etc.) are known in the art. Measurement of, for example, residual stress is an important consideration when designing devices. For example, residual stresses can affect the mechanical performance (e.g., static and fatigue strength, fracture toughness, corrosion-/wear-resistance, etc.) and thus the reliability of components and devices. Residual stresses can be introduced by, for example, thermal mismatch or mechanical/thermal processing during the manufacturing, welding, and sintering operations. In a thin-film system, residual stresses have been generated from, for example, a thermal expansion mismatch between a film and a substrate during cooling in a deposition process. In welded metals, residual stresses have been caused by the welding thermal cycle due to heterogeneous heating and cooling. Residual stresses have resulted also from crystalline mismatches (e.g., face-centered cubic material in contact with body-centered cubic material, etc.).

Methods for the measurement of residual stresses have included mechanical stress-relaxation methods (e.g., hole drilling technique, saw cutting technique, curvature measurement method for a film/coding system, layer removal technique, etc.) and physical-parameter analysis methods (e.g., analysis of x-ray diffraction, ultrasonic wave, magnetic Barkhausen noise, neutron diffraction, and Raman spectra, etc.). However, mechanical stress-relaxation methods have been limited in application due to the destructive nature of the method. Physical-parameter analysis methods have been limited in application due to the requirement of the preparation of stress-free reference samples for comparison purposes. Moreover, physical methods have generally not been useful in determining residual stress of amorphous/glass materials that do not have a long-range ordered atomic structure. See, e.g., JANG, "Estimation of residual stress by instrumented indentation: A review," Journal of Ceramic Processing Research, Vol. 10, No. 3, 391-400 (2009).

With instrumented indentation (e.g. nanoindentation, etc.), it has been possible to measure a variety of mechanical properties (e.g., hardness, Young's modulus, yield strength, work-hardening exponent, creep stress exponent, fracture toughness, and small-scale mechanical behavior, etc.) by analyzing the indentation load-displacement curve without the need to observe a hardness impression using microscopy.

Existing systems for measuring material properties such as residual stress, however, frequently require a zero-stress reference sample (which may be difficult to obtain), evaluation of indentation contact area, and/or separate expensive testing systems (e.g., microscopy, indentation, etc.).

Consequently, there remains a need in the material property measurement industry to efficiently measure residual stress and other properties without the requirement of a separately manufactured zero-stress reference sample. In particular, there remains a need for accurately, efficiently, and reproducibly measuring residual stresses of various materials.

Some publications discussing various aspects of measurement of residual stress and/or indentation include: BOCCIARELLI et al. "Indentation and imprint mapping method for identification of residual stresses," Computational Materials Science 39 (2007) 381-392; FAISAL et al., "A Review of Patented Methodologies in Instrumented Indentation Residual Stress Measurements," 2011, 4, 138-152; JANG et al., "Assessing welding residual stress in A335 P12 steel welds before and after stress-relaxation annealing through instrumented indentation technique," Scripta Materialia 48 (2003) 743-748; JANG, "Estimation of residual stress by instrumented indentation: A review," Journal of Ceramic Processing Research, Vol. 10, No. 3, 391-400 (2009); PONSLET et al., "Residual Stress Measurement Using The Hole Drilling Method And Laser Speckle Interferometry Part III: Analysis Technique," Experimental Techniques, September/October 2003; 45-48; SURESH et al., "A New Method For Estimating Residual Stresses By Instrumented Sharp Indentation," Acta Materialia, Vol. 46, No. 16, 5755-5767; Vishay Precision Group, "Measurement of Residual Stresses by the Hole-Drilling Strain Gage Method," Tech Note TN-503, document number: 11053; revision: Nov. 1, 2010; www.micromeasurements.com; 19-33; XU et al., "Chapter 7: Residual Stress Determination Using Nanoindentation Technique," Micro and Nano Mechanical Testing of Materials and Devices; Editors: Yang et al.; Springer Science+Business Media, LLC, 2008; doi: 10.1007/978-0-387-78701-5, 139-153; XU, "Estimation of residual stresses from elastic recovery of nanoindentation," Philosophical Magazine, Vol. 86, No. 19, Jul. 1, 2006, 2835-2846; XU et al., "Influence of equi-biaxial residual stress on unloading behaviour of nanoindentation," Acta Materialia, 53, (2005) 1913-1919, each of which is incorporated herein by reference in its entirety.

Some patents and patent publications discussing various aspects of measurement of residual stresses and/or indentation include U.S. Pat. No. 6,155,104 (Suresh et al.); U.S. Pat. No. 6,311,135 (Suresh et al.); U.S. Pat. No. 6,568,250 (Sinha); U.S. Pat. No. 6,851,300 (Kwon et al.); U.S. Pat. No. 7,472,603 (Kim et al.), U.S. Pat. Appl. Pub. Nos. 2007/0180924 (Warren et al.), 2007/0227236 (Bonilla et al.), 2010/0064765 (Han et al.), 2010/0108884 (Lou et al.), and Int'l PCT Pat. Appl. Pub. Nos. WO 2006/071001 (Kim) and WO 2008/096914 (Han), each of which is incorporated herein by reference in its entirety.

All patents and patent applications (e.g., from the United States or elsewhere) and all other published documents mentioned anywhere in this application are incorporated herein by reference, each in its entirety, as if fully reproduced herein.

Without limiting the scope of the present disclosure, a brief summary of some of the claimed embodiments is set forth below. Additional details of the summarized embodiments and/or additional embodiments of the present disclosure may be found in the Detailed Description of the Invention below.

A brief abstract of the technical disclosure in the specification is provided as well only for the purposes of complying with 37 C.F.R. § 1.72. The abstract is not intended to be used for interpreting the scope of the claims.

SUMMARY

In one or more aspects of the present disclosure, a method (e.g., a method measuring residual stress of a sample, etc.) may include indenting a first portion of a sample (e.g., a measurement zone) having residual stress and generating a residual stress reference zone (e.g., a zero-stress reference zone) at a second portion of the sample.

In one or more embodiments, the method further includes indenting the sample in the residual stress reference zone. For example, the method may include making two or more indentations in the residual stress reference zone. In one or more embodiments indenting the sample in the residual stress reference zone includes generating a load-displacement curve in the residual stress reference zone for the purpose of comparing to a load-displacement curve generated in a measurement zone of the sample. In one or more embodiments measuring the residual stress in a given zone may include making a plurality of indentations in a measurement zone of the sample and generating a composite load-displacement curve.

In one or more embodiments, generating the residual stress reference zone includes removing material from the sample and/or effecting a local microstructural change or thermal-mechanical effect. Removing material from the sample may be performed using any of a wide variety of techniques known in the art. For example, removing material from a sample may include using a drill to form a through hole. In one or more embodiments, removing material from a sample may include raster scanning with the use of an indenting device (e.g., an indenter, nanoindenter, etc.). In one or more embodiments, removal of material from a sample may include contacting the sample with one or more forms of energy and/or one or more particles. Embodiments of the present disclosure may include any technique for removing material from the sample (e.g., to generate a residual stress reference zone) including, but not limited to, abrading, grinding, cutting, drilling, etc.

Effecting a local microstructural change or thermal mechanical effect in a sample or sample surface may include interacting (e.g., processing, etc.) with a sample surface by directing toward the surface a quantity of energy (e.g., a beam, etc.) and/or contacting the surface with particles (e.g., particle bombardment, electrons, etc.). In one or more embodiments, a local microstructural change or thermal mechanical effect in the sample may be effected by way of one or more of the following techniques: electron-beam microscopy, scanning probe microscopy (SPM), scanning electron microscopy (SEM), transmission electron microscopy (TEM), and exposing the sample to one or more forms of energy including, but not limited to, laser energy, ion beam energy, heat energy (e.g., annealing, etc.), vibration energy, and ultrasonic energy (e.g., sound energy, etc.).

In one or more embodiments, generating the residual stress reference zone includes forming a feature in the sample, wherein the feature includes a hole or a flat-treated portion of the surface of the sample. For example, removing material from the sample may include forming a hole (e.g., a cavity, etc.) in the sample, wherein the hole extends partially or entirely through the sample. In some embodiments, a hole may extend through one or more layers (e.g., one or more coatings, etc.) of the sample. For example, a hole may extend through one or more layers of coating disposed on a substrate.

In the present disclosure, a "hole" in a sample refers to a volume from which a quantity of material has been removed from the sample. Put another way, the sample surface may define an opening having a perimeter, from which one or more sidewalls extend into the sample and terminate at a second opening at the opposite side of the sample (e.g., a through hole, an aperture, etc.) or at a bottom surface extending between the one or more sidewalls (a blind hole, etc.). The sidewalls define a volume (e.g., a hole, a cavity, a void, a hollow space, etc.).

In one or more embodiments of the present disclosure wherein generating the residual stress reference zone includes the formation of a hole, the hole may have a depth in the range of from 0.001% to 100% of the sample depth (e.g., thickness).

In one or more methods of the present disclosure, the method includes disposing the sample to be tested on an instrument platform of an indenting device. In one or more embodiments, the indenting of the sample and the generating of the residual stress reference zone occur on the instrument platform (e.g., the same instrument platform). In some embodiments, the indenting of the sample and the generating of the residual stress reference zone are performed by the same apparatus and may, for example, both occur without moving the sample relative to the instrument platform (e.g., in situ).

In one or more embodiments, the method includes measuring the magnitude of the residual stress. Measuring the magnitude of the residual stress may occur in any of a wide variety of methods known in the art. For example, determining the magnitude of the residual stress may include generating a loading and unloading curve resulting from indentation testing of the sample. The loading and unloading curve may be analyzed to determine the magnitude of the residual stress.

In one or more embodiments of the present disclosure, a method may include transporting an apparatus, including an indenter device and a reference-generating device, to the location of the sample. In other words, the indenting of the first portion of a sample having a residual stress and generating a residual stress reference zone at a second portion of the sample may be accomplished after transporting a portable apparatus to a sample in the field. Thus, the one or more embodiments of the present disclosure may be useful for the evaluation of materials that are not easily transported.

In one or more embodiments, the indentation in the first portion of the sample is separated from the residual stress reference zone by a distance sufficient to avoid influencing the residual stress in the first portion by the presence of the residual stress reference zone. In one or more embodiments, such a distance may be at least 10 micrometers (μm) (e.g., at least 20 μm, at least 50 μm, at least 100 μm, at least 500 μm, at least 1000 μm, at least 10,000 μm, etc.). In some embodiments such a distance may be 1000 μm or less, 100 μm or less, 20 μm or less, etc.

In one or more aspects of the present disclosure, an apparatus (e.g., an apparatus for measuring residual stress of a sample, etc.) may include an indenter device structured and arranged to indent a first portion of a sample and a reference-generating device structured and arranged to generate a residual stress reference zone in the sample. In one or more embodiments, the apparatus is structured and arranged to both indent the sample and generate the reference sample in situ. In some embodiments, the indenter is a nanoindenter.

In some embodiments, the apparatus further includes a platform on which the sample may be disposed. In such embodiments, the apparatus may also include a translation device to move the platform and/or the indenter device in one or more dimensions (e.g., spatial, angular, etc.). In some embodiments, a translation device may move and/or position the platform with one, two, or three spatial degrees of freedom (e.g., translation in one or more of the X-, Y-, and/or Z-axes) and three rotational degrees of freedom (e.g., rotation about one or more of the X-, Y-, and/or Z-axes). Similarly, in some embodiments, a translation device may move and/or position the indenter device and/or the reference-generating device with one, two, or three spatial degrees of freedom (e.g., translation in one or more of the X-, Y-, and/or Z-axes) and one, two, or three rotational degrees of freedom (e.g., rotation about one or more of the X-, Y-, and/or Z-axes).

In one or more aspects of the present disclosure, a method for generating a residual stress reference may include providing a sample (e.g., a first sample, etc.) including a residual stress and reducing the residual stress in at least a portion of the sample. In one or more embodiments, reducing the residual stress includes at least one of the following techniques: raster scanning wear using an indenter (e.g., a nanoindenter, etc.), electron beam microscopy, scanning probe microscopy, scanning electron microscopy, and exposing the sample to one of the following forms of energy: laser energy, ion beam energy, heat energy, vibration energy; and ultrasonic energy. In some embodiments, reducing the residual stress includes eliminating the residual stress in at least the portion of the sample.

In some embodiments, the method may further include providing a second sample (e.g., in addition to the first sample), wherein the first and second samples are similarly formed (e.g., manufactured, processed, etc.), and indenting the second sample. In one or more embodiments, the method also includes determining the residual stress (e.g., the magnitude of the residual stress) of the second sample. In some embodiments, providing the first sample includes disposing the first sample on a platform of an indentation device and providing the second sample includes disposing the second sample on the platform of the indentation device. In one or more embodiments, the second sample may be the same as or different from (e.g., separate from) the first sample.

DEFINITIONS

As used herein, "and/or" in conjunction with a list of items means any one or more of the items in the list joined by "and/or". For example, "x and/or y" means any element of the three-element set {(x), (y), (x, y)}. For another example, "x, y, and/or z" means any element of the seven-element set {(x), (y), (z), (x, y), (x, z), (y, z), (x, y, z)}.

As used herein, the term "exemplary" means serving as a non-limiting example, instance, or illustration. As used herein, the terms "e.g.," and "for example," introduce a list of one or more non-limiting embodiments, examples, instances, and/or illustrations.

BRIEF DESCRIPTION OF THE FIGURES

The present disclosure, including the following detailed description of certain embodiments, can be understood with reference to the following figures:

FIGS. 4A and 4B depict a schematic representation of a top (FIG. 4A) and a cross-sectional (FIG. 4B) view of each of four exemplary test samples after in situ generation of a zero-stress reference zone in accordance with one or more embodiments of the present disclosure.

Drawings are not necessarily to scale.

DETAILED DESCRIPTION

Residual stress generated due, for example, to the strain or thermal stress imposed on a material causes several problems, such as the deterioration of mechanical properties including the fatigue strength and destructive material property of a material and the like, and difficulty of post-processing. In the case of a thin-film material, residual stress generated at an interface between different materials may be an important factor influencing mechanical integrity. For bulk materials, the importance of residual stress generated during welding is well known. Conventional methods of measuring residual stress include hole drilling, saw cutting, x-ray diffraction, Barkhausen magnetic noise measurement, ultrasonic techniques, and neutron diffraction. Indentation and nanoindentation techniques have also been used and generally employ analysis and/or comparison of loading and unloading curves of a sample having a residual stress and a separate zero-stress reference sample.

An object of the present disclosure is to provide a method and apparatus for measuring residual stress, wherein the methods and apparatuses are widely applied to fields ranging from a nanoscopic area to a macroscopic structure. Another object of the present disclosure is to provide a method and apparatus for measuring residual stress using indentation without the requirement of provision of a separate reference sample. Another object of the present disclosure is to provide a method and apparatus capable of measuring residual stress of a sample using indentation (e.g., nanoindentation, etc.) with in situ reference generation.

In one or more embodiments, the methods and apparatuses described herein may be useful for measuring residual stress using indentation (e.g., on a macro-, micro-, and/or nano-scale, etc.) with an in situ generated reference. Any of a wide variety of samples may be tested with the one or more embodiments of the methods and apparatuses described herein. Samples may include items having a dimension on the nano-scale (e.g., nanotubes, nanowires, nanorings, nanocomposites, etc.), a micro-scale (e.g., thin-film systems, MEMS (micro-electromechanical systems) devices, read/write heads, integrated circuits (IC), semiconductor devices, etc.), or on a macro-scale (e.g., welds, etc.). As used herein, "nano-scale" refers to a dimension that is from 1 nanometer (nm) to less than 1 micrometer (μm), "micro-scale" refers to a dimension that is from 1 micrometer to less than 1 millimeter (mm), and "macro-scale" refers to a dimension that is at least 1 millimeter. Any of a wide variety of materials (e.g., metals, metal oxides, nonmetals, metalloids, ceramics, semi-metals, crystalline, natural, synthetic, composites, etc.) may be tested using one or more of the embodiments of apparatuses and methods of the present disclosure.

Figure 1:
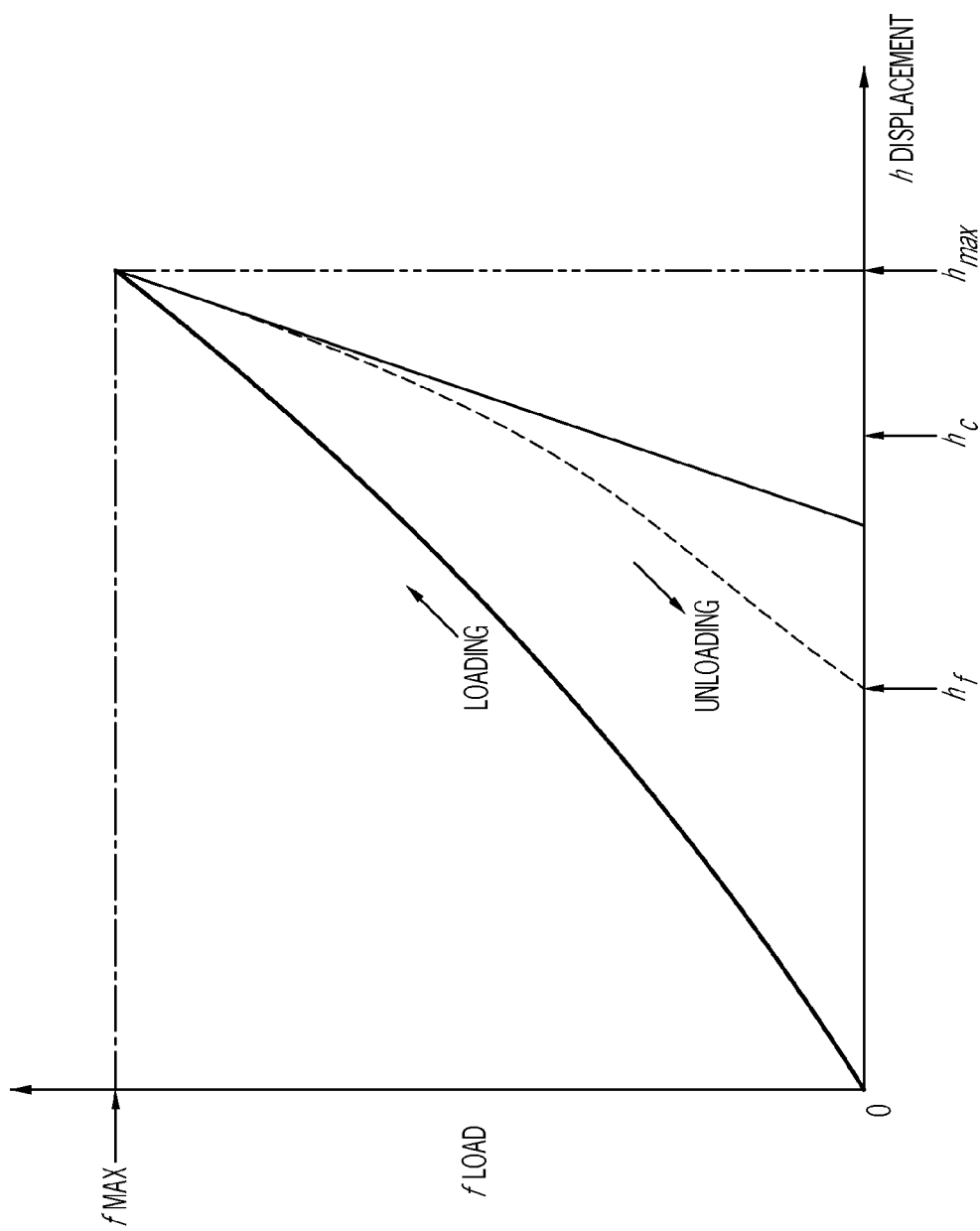
FIG. 1 depicts a representative schematic of a load-displacement curve (e.g., loading curve, unloading curve, etc.).

Measuring residual stress may include creating an indentation load versus displacement curve of a sample. FIG. 1 depicts a typical load-displacement curve of an indentation made with an indenter (e.g., a sharp indenter). At the beginning of the test, the indenter tip contacts the sample at the origin of the graph in FIG. 1. Both load and displacement are measured throughout the determination of the loading and unloading curve. As the load increases, the indenter tip progressively displaces further into the material sample up to a maximum displacement at $h_{max}$ corresponding to a maximum load $f_{max}$. Then, the load on the indenter tip is reduced down to no load, resulting in the unloading curve in FIG. 1, which ends at $h_f$ representing the final displacement. Generally, $h_f$ represents the magnitude of plastic deformation of the sample due to the indentation, whereas the difference between $h_{max}$ and $h_f$ represents the elastic recovery of the sample. When $h_f$ is greater than zero, then the indentation process results in an indentation mark caused by the plastic deformation of the sample.

From the loading and unloading curves, a number of determinations may be made. For example, indentation hardness of the sample can be determined by dividing the maximum load by the projected contact area of the indentation (e.g., which may be determined as a geometric function of the contact depth $h_c$, by a popular method proposed by Oliver and Pharr, etc.). The Oliver and Pharr method includes a geometric parameter based on the shape of the indentation tip and the stiffness S that can be measured as the initial slope of the unloading curve, which is represented by the tangent line in FIG. 1 extending from the point of maximum load/displacement to the displacement axis. In FIG. 1, $h_c$ represents an estimation of contact depth, which may be determined based on a theoretical model from Oliver and Pharr. In one or more embodiments, a curve of indentation load versus penetration displacement, similar to that shown in FIG. 1, may be generated for a sample in either a measurement zone and/or a residual stress reference zone.

Figure 2:
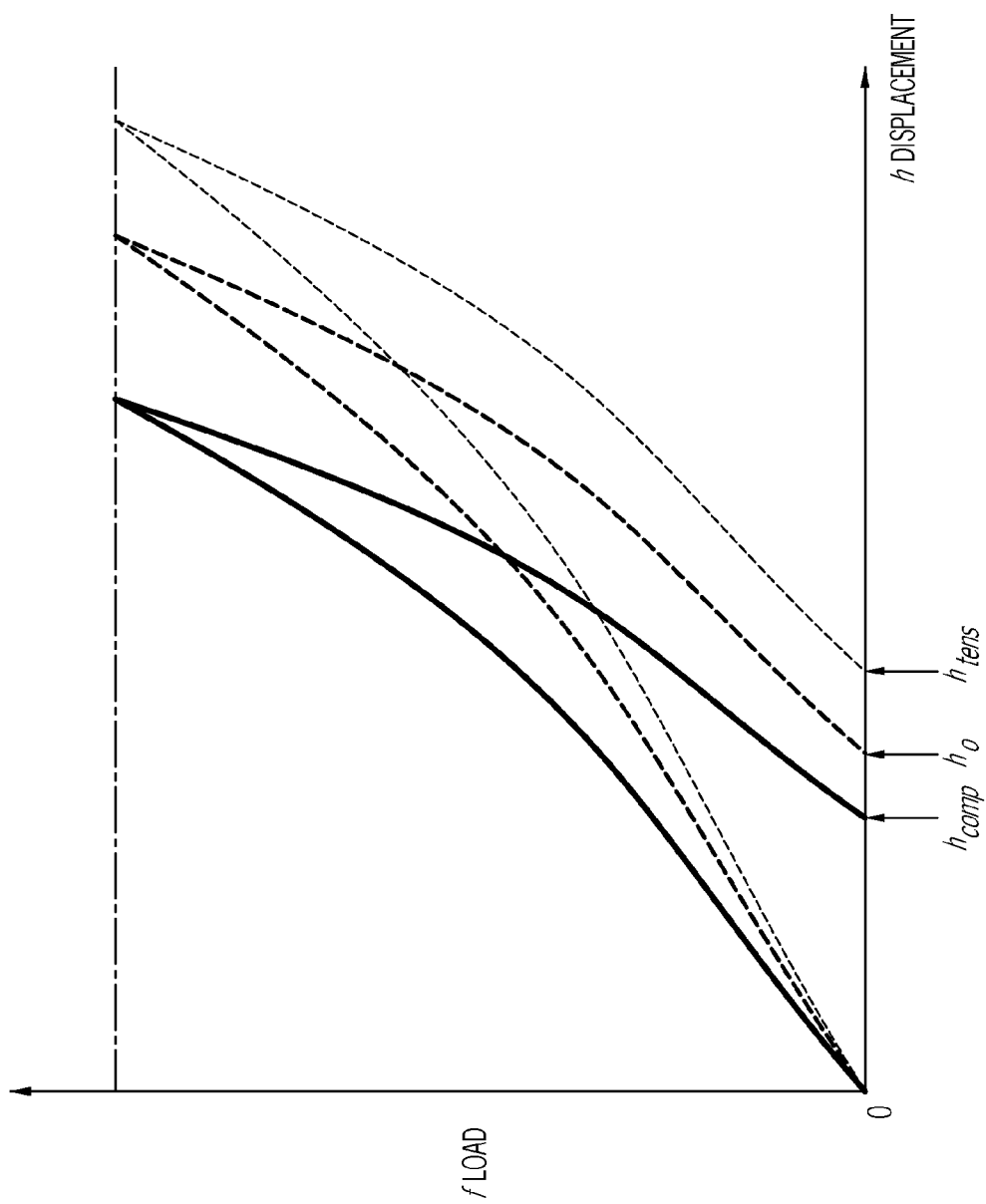
FIG. 2 depicts a schematic of comparative load-displacement curves (e.g., loading curve, unloading curve, etc.) for three residual stress states: compressive, zero-stress, and tensile.

It has been reported that one may estimate the residual stress of a sample by analyzing the deviation and shape of the indentation curve from the ideal shape. For example, FIG. 2 depicts the loading and unloading curves of three samples including a sample subject to compressive residual stress (ending at $h_{comp}$), a sample subject to zero residual stress (ending at $h_0$), and a sample subjected to tensile residual stress (ending at $h_{tens}$). As can be seen from FIG. 2, for a given maximum load, $f_{max}$, a compressive residual stress shifts the loading and unloading curves to the left, whereas a tensile residual stress shifts the loading and unloading curves to the right, each relative to the loading and unloading curves of a zero-stress reference sample. Thus, based on a comparison of the loading and unloading curve of a zero stress reference sample, a determination may be made as to the compressive or tensile nature of a residual stress of a sample as well as the magnitude of the residual stress.

Various models have been proposed for estimating the residual stress of a sample based on this type of comparison. Jang provided a review of various estimation methods in 2009. See JANG, "Estimation of residual stress by instrumented indentation: A review," Journal of Ceramic Processing Research, Vol. 10, No. 3, 391-400 (2009). Many such methods require the need for a separate stress-free reference sample. However, a reference sample should have a microstructure almost identical to the test specimen, which may be difficult to achieve, especially in a material having significant microstructural gradient and/or a material in a thin-film system where, for example, annealing can relax the residual stresses of a thin film, thereby changing the microstructure and the intrinsic mechanical properties.

The one or more embodiments of the present disclosure may employ any of a wide variety of models and techniques (e.g., as described in the literature and patent documents cited herein, etc.) for determining residual stress that include indentation and/or loading/unloading curves.

Figure 3:
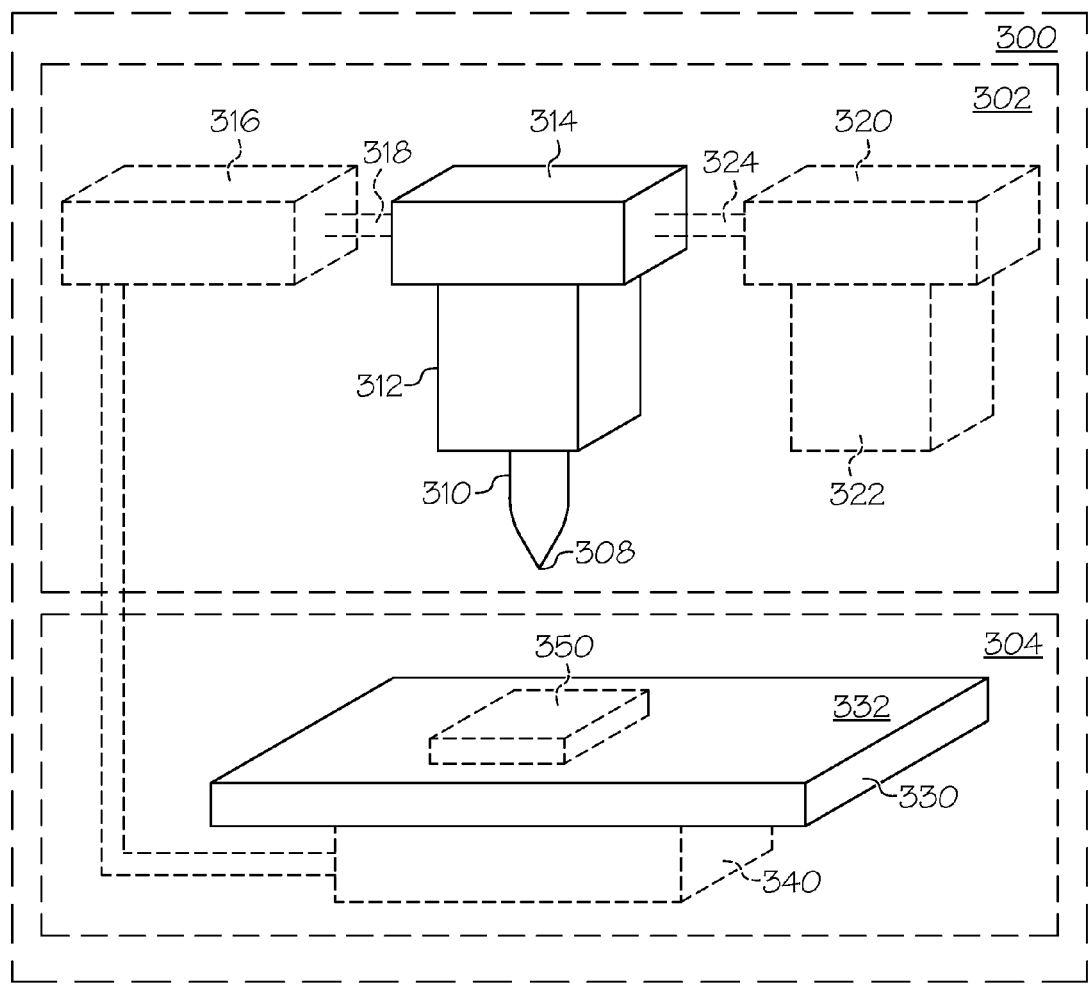
FIG. 3 depicts a schematic of an apparatus in accordance with one or more embodiments of the present disclosure.

With regard to FIG. 3, an apparatus 300 (e.g., for measuring the residual stress of a sample with in situ reference generation, etc.) may include a measuring system 302. The measuring system 302 may include an indenter device 312 (e.g., a microindenter device, a nanoindenter device, etc.) structured and arranged to indent a first portion of a sample 350 and a reference-generating device 322 structured and arranged to generate a residual stress reference zone in the sample 350. In some embodiments, the apparatus 300 may indent the sample and generate a reference sample in situ. Indenter device 312 includes an indenter 310 having an indenter tip 308.

In one or more embodiments, the reference generating device 322 may be incorporated in the indenter device 312. For example, in an embodiment in which the reference-generating device includes a raster-scanning wear system utilizing an indenter, the reference generating device 322 may itself be embodied in indenter device 312 and may utilize indenter 310 with indenter tip 308.

Apparatus 300 of FIG. 3 may also include a platform system 304 that includes a platform 330 having a platform surface 332. In some embodiments, sample 350 may be disposed on the platform surface 332 for in situ reference generation and indentation testing. Platform system 304 may include a platform translation device 340 for translating the platform in one, two, or three spatial dimensions (e.g., X-, Y-, and/or Z-axis) and/or rotation about one, two, or three axes of rotation (e.g., rotation about the X-, Y-, and/or Z-axis, etc.). In this manner, any desired orientation of sample 350 is possible.

Similarly, apparatus 300 may be structured and arranged to accommodate any desired orientation of indenter device 312 and/or reference generating device 322. For example, apparatus 300 of FIG. 3 may include a translation device 316 for translating the indenter device 312 and/or the reference-generating device 322 in one, two, or three spatial dimensions (e.g., X-, Y-, and/or Z-axis) and/or rotation about one, two, or three axes of rotation (e.g., rotation about the X-, Y-, and/or Z-axis, etc.). Translation of the indenter device 312 and/or the reference-generating device 322 may be accomplished via mechanical and/or electrical engagement of the indenter device translation system 314 and/or the reference-generating device translation system 320 via connectors 318, 324 (e.g., mechanical and/or electrical connectors, etc.). Any of a wide variety of translation devices (including, e.g., mechanical and electrical connectors and controls) may be used in the present disclosure. In one or more embodiments, movement of the indenter device 312 may be dependent on or independent of the movement of the reference generating device 322. In some embodiments, only one of the platform 330 and the indenter may be translated.

In one or more embodiments of the present disclosure, a residual stress reference may be generated by providing a first sample having a residual stress and reducing such residual stress in at least a portion of the sample. In other embodiments, reducing the residual stress may effect an at least 10% reduction of residual stress (e.g., at least 25%, at least 50%, at least 75%, at least 90%, at least 95%, at least 99%, at least 99.9% reduction of residual stress, 100% reduction of residual stress, etc.).

For example, reducing the residual stress may include changing the structure of a sample by, for example, forming a hole (e.g., a through hole, a blind hole, a hole in a layer, etc.) in the sample. For example, FIG. 4A depicts the top view of a sample 400a having a surface 402a in which a hole 404a has been formed (e.g., for the purpose of generating a residual stress reference zone). As shown in FIG. 4B, hole 404a in sample 400a is a through hole (i.e., hole 404a extends for a depth of 100% of the sample thickness).

Reference generation may be accomplished in one or more embodiments by the formation of a blind hole. For example, sample 400b having a surface 402b includes a hole 404b that extends from surface 402b for a depth of less than 100% of the sample thickness (see FIG. 4B).

In some embodiments, a hole has a depth, as a percentage of sample thickness, in the one or more of the following ranges: from 0.001% to 50%, from 0.001% to 10%, from 0.001% to 1%, from 0.001% to 0.1%, at least 1%, at least 10%, at least 25%, at least 50%, up to 10%, up to 1%, up to 0.1%, up to 0.01%. Although the holes 404a and 404b are shown as cylindrical (e.g., circular with a flat bottom), it should be noted that any of a wide variety of hole shapes may be used including, but not limited to, geometric and irregular shapes. In the present disclosure, holes may have any dimensions without limitation. However, in one or more embodiments of the present disclure, the diameter of a hole may be at least 1 angstrom and up to 1 mm (e.g., up to 100 micrometers, up to 10 µm, up to 1 µm, up to 100 nm, up to 10 nm, etc.), preferably from about 1 micrometer to about 10 micrometers (e.g., from about 1 micrometer to about 2 micrometers).

In some embodiments, reference generation may be accomplished by the formation of a hole in one or more layers of a sample. For example, sample 400c includes sample surface 402c formed from a coating of a first material that is disposed on a substrate 406 formed from a second material. In one or more embodiments, a reference may be generated by removing a portion of the coating from the underlying layers of material and/or substrate. In the embodiment of FIGS. 4A and 4B, hole 404c represents a complete removal of the coating from at least a portion of sample 400c.

In the present disclosure, removal of material in order to form a residual stress reference zone may be accomplished by any of a wide variety of known material removal methods including, but not limited to, raster scanning wear using an indenter and exposing the sample to laser energy; exposing the sample to ion beam energy, exposing the sample to electron beam microscopy, exposing the sample to scanning probe microscopy, and exposing the sample to scanning electron microscopy.

Raster scanning may include scanning an indentation tip across the sample using a light load. In some cases raster scanning can include continuous measurement of displacement and load and can be conducted without damaging the sample. In one or more embodiments, raster scanning may be employed to remove one or more layers of the sample surface by translating the indenter tip across the sample surface. Raster scanning generally includes movement of an indenter tip along a path (e.g. a zigzag motion, a serpentine motion, along a grid, etc.) in order to remove a relatively thin layer of material (e.g., the thickness of the material removed is relatively small (e.g., less than 50% of, less than 10% of, less than 1% of, etc.) compared to the dimensions of the area of the material removed). In one or more embodiments raster scanning includes removal of material from an area where in the resultant hole has a constant depth. In one or more embodiments, raster scanning may include use of a piezo scanner, wherein application of or increasing voltage (or reduction of same) to the piezo scanner results in expansion or contraction of the piezo to generate the movement of the raster scanner.

In some embodiments, a reference may be generated without removal of material from a sample. For example, sample 400d having surface 402d includes a treated portion 404d that has been subjected to a treatment sufficient to reduce or eliminate residual stresses in at least a portion of the surface 402d of sample 400d. For example, residual stresses may be reduced or eliminated without removing material by, for example, exposing the sample to heat energy, vibration energy, and/or ultrasonic energy.

Figure 5:
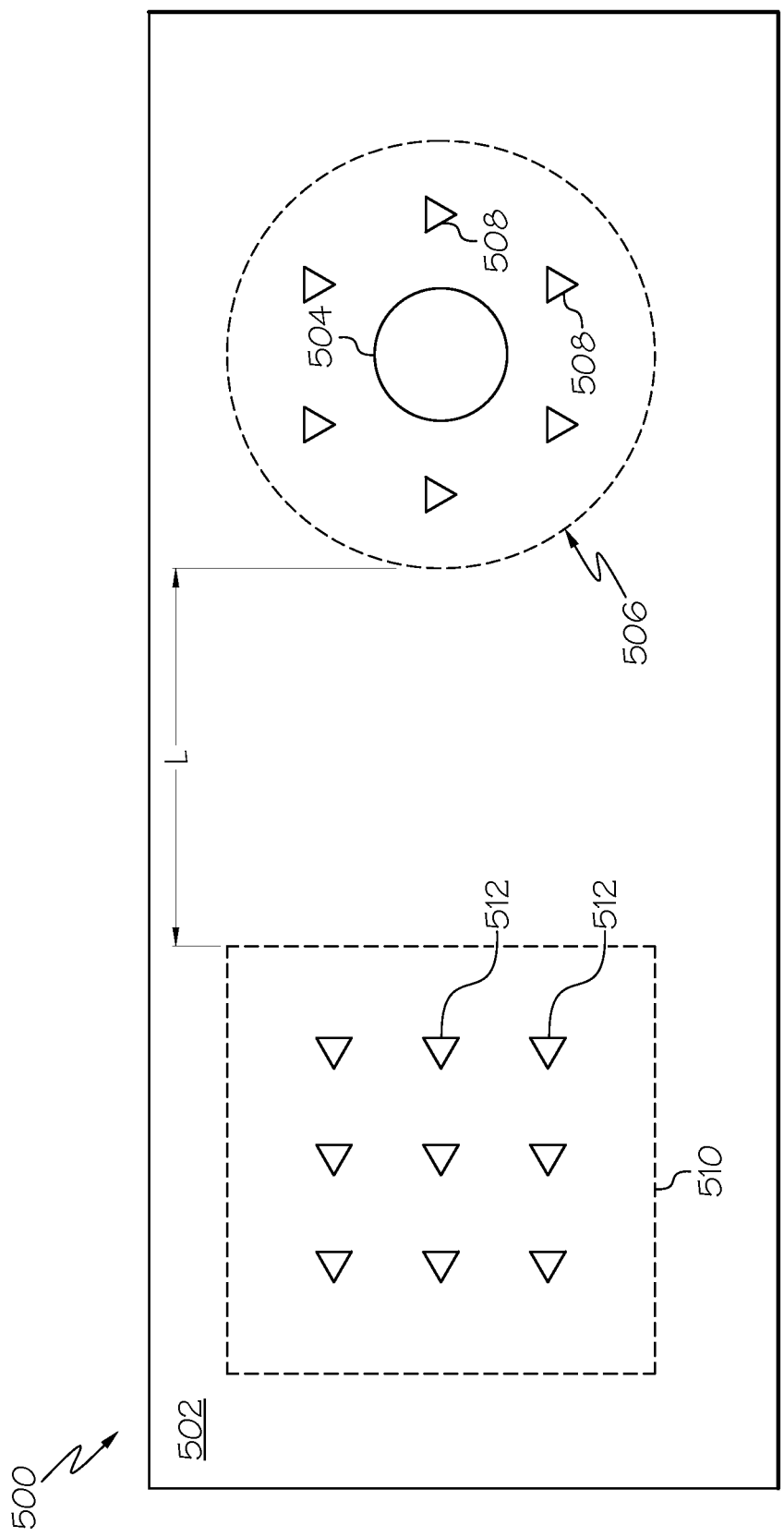
FIG. 5 depicts a schematic representation of a top view of a test sample after indentation testing inside and outside of a zero-stress reference zone in accordance with one or more embodiments of the present disclosure.

With regard to FIG. 5, sample 500 is depicted having a sample surface 502. A residual stress reference zone 506 has been generated on the surface of sample 500 by the formation of hole 504. Of course, as described herein, a residual stress reference zone may be generated, in some embodiments, without formation of a hole.

In the residual stress reference zone 506, indentation testing may occur (as shown by indentation marks 508) for the purpose of generating a reduced-stress or zero-stress loading and unloading curve as shown in FIG. 2. Moreover, indentation testing of sample 500 may be conducted outside of the residual stress reference zone 506, as shown by indentation marks 512 in measurement zone 510. It should be noted that any number of indentations (e.g., one or more, two or more, etc.) may be made in the reference zone and measurement zone. In some embodiments, the measurement zone 510 is separated from the residual stress reference zone 506 by a distance L sufficient to avoid influencing the residual stress in the first portion by the presence of the residual stress reference zone.

Although the indentation marks 508 in the residual stress reference zone 506 are shown in FIG. 5 as being symmetric about hole 504, this is not required. However, indentation marks 508 may be sufficiently close to hole 504 to provide a reproducible load-displacement curve representative of a zero stress reference sample. In one or more embodiments, the indentation marks 508 may be located within three indentation diameters of the hole 504. In some embodiments, the indentation marks 508 may be located in excess of three indentation diameters of the hole. Similarly, although the indentation marks 512 in the measurement zone 510 are shown in FIG. 5 as being in a grid (e.g., a square grid or pattern), this is not required. However, indentation marks 512 may be sufficiently distant from hole 504 to provide a reproducible load-displacement curve representative of the residual stress of sample 500.

In some applications where residual stress testing is desired, the sample may be too small to allow reference generation and indentation of the same sample. In one or more embodiments, a method may include reducing the residual stress in at least a portion of a first sample for generation of a residual stress reference zone and may further include providing a second sample, wherein the first and second samples are similarly formed, and indenting the second sample. For example, the first and second samples may be indented for the generation of a load displacement curve for each, for the purpose of determining the residual stress of the second sample. In some embodiments the first and second sample may be disposed on the same platform of an indentation device (e.g., in situ). In one or more embodiments, the second sample may be connected to or may be separate from the first sample.

In one or more embodiments, the material being tested while it is under observation, wherein observation may be conducted via optical microscopy, electron beam microscopy, transmission electron microscopy, scanning electron microscopy, atomic force microscopy, etc.

It may be noted that any of a wide variety of indenters (e.g., nanoindenter) may be used in the one or more embodiments of the present disclosure. For example, in some embodiments, the nanoindenter is a quantitative nanoindenter. In some embodiments, the nanoindenter includes a cube corner nanoindenter tip (e.g., blunt, sharp, etc.). Other various embodiments of nanoindenters suitable for use in the devices and methods of the present disclosure include, but are not limited to, a round end cone nanoindenter, a filament rod nanoindenter, a Berkovich nanoindenter (e.g., 3-sided pyramidal), a Vickers nanoindenter, and a Knoop nanoindenter. Nanoindenter tips may be, for example, pyramidal, wedge-shaped, cone-shaped, cylindrical, spherical, or filament-like. In some cases, positional resolution of nanoindenters can be as precise as plus or minus 0.1 nm. In some embodiments, a nanoindenter may include a step motor with a resolution of less than 15 nanometers.

Various aspects of the present disclosure are depicted in the figures. Elements depicted in one figure may be combined with and/or substituted for elements depicted in any other figure, as may be desired by one of ordinary skill in the art.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A method of measuring residual stress using an instrument platform comprising:
   indenting a first portion of a sample having residual stress; and
   generating a residual stress reference zone at a second portion of the sample, the residual stress reference zone creating a reduced-stress or zero-stress portion of the sample;
   the indenting of the first portion and the generating of the residual stress reference zone both being done in situ, on the same instrument platform, and
   comparing the indented first portion with the generated residual stress reference zone to determine the residual stress of the sample.

2. The method of claim 1, further comprising indenting the sample in the residual stress reference zone.

3. The method of claim 1, wherein generating the residual stress reference zone comprises removing material from the sample and/or effecting a local microstructural change or thermal-mechanical effect to produce the reduced-stress or zero-stress portion of the sample.

4. The method of claim 3, wherein removing material and/or effecting a local microstructural change or thermal-mechanical effect comprises one or more of the following techniques:
   raster scanning wear using an indenter;
   exposing the sample to laser energy;
   exposing the sample to ion beam energy;
   exposing the sample to electron beam microscopy;
   exposing the sample to scanning probe microscopy;
   exposing the sample to scanning electron microscopy;
   exposing the sample to heat energy;
   exposing the sample to vibration energy; and
   exposing the sample to ultrasonic energy.

5. The method of claim 1, further comprising measuring the magnitude of the residual stress.

6. The method of claim 5, wherein measuring the magnitude of the residual stress comprises generating a loading and unloading curve.

7. The method of claim 1, further comprising transporting an apparatus comprising an indenter device and a reference-generating device to the location of the sample.

8. The method of claim 1, wherein generating the residual stress reference zone comprises forming a feature of the sample, wherein the feature comprises a hole or a flat-treated portion of the surface.

9. The method of claim 1, wherein the first and second portions are separated by a distance sufficient to avoid influencing the residual stress in the first portion by the presence of the residual stress reference zone.

10. An apparatus for measuring residual stress comprising:
    an indenter device structured and arranged to indent a first portion of a sample;
    a measurement device for measuring the residual stress of the sample;
    a reference-generating device structured and arranged to generate a residual stress reference zone in the sample, the residual stress reference zone creating a reduced-stress or zero-stress portion of the sample for comparison with the indented first portion, to measure the residual stress of the sample,
    the indenter device and the reference-generating device both being on an instrument platform so that both the indenting of the first portion of the sample and the generating the residual stress reference zone are done in situ.

11. The apparatus of claim 10, wherein the indenter is a nanoindenter.

12. The apparatus of claim 10, wherein apparatus includes a translation device to move the platform and/or the indenter device in one or more spatial dimensions.

13. A method for generating a residual stress reference, the method comprising:
providing a first sample comprising a residual stress in a first portion of the sample;
reducing the residual stress in at least a second portion of the sample, to create a reduced-stress or zero-stress second portion of the sample for comparison with the first sample;
comparing the first portion with the reduced-stress or zero-stress second portion of the sample to determine the residual stress of the sample;
the first portion of the sample having the residual stress and the reducing the residual stress in at least a second portion of the sample being done in situ, on an instrument platform, and
wherein reducing the residual stress comprises at least one of the following techniques:
raster scanning wear on an indenter, wherein the indenter may optionally be a nanoindenter;
exposing the sample to laser energy;
exposing the sample to ion beam energy;
exposing the sample to electron beam microscopy;
exposing the sample to scanning probe microscopy;
exposing the sample to scanning electron microscopy;
exposing the sample to heat energy;
exposing the sample to vibration energy; and
exposing the sample to ultrasonic energy.

14. The method of claim 13, wherein reducing the residual stress comprises eliminating the residual stress in at least the portion of the sample.

15. The method of claim 13, further comprising:
providing a second sample, wherein the first and second samples are similarly formed.

16. The method of claim 15, wherein the second sample is separate from the first sample.

* * * * *